United States Patent [19]

Fenelli

[11] Patent Number: 5,107,026
[45] Date of Patent: Apr. 21, 1992

[54] FLUORINATED ACETYLENE-CONTAINING AROMATIC AMINES AND DIAMINES

[75] Inventor: Steven P. Fenelli, Hillsborough, N.J.

[73] Assignee: National Starch and Chemical Investment Holding Corporation, Wilmington, Del.

[21] Appl. No.: 631,132

[22] Filed: Dec. 20, 1990

[51] Int. Cl.$^5$ .................. C07C 205/12; C07C 211/43
[52] U.S. Cl. ...................................... 564/441; 564/442
[58] Field of Search ................................ 564/442, 441

[56] References Cited

U.S. PATENT DOCUMENTS 4,594,352  6/1986  Massardo et al. .................... 514/332

OTHER PUBLICATIONS

Acardi et al., *Chem. Abs.* 112:35620K (1990).

*Primary Examiner*—Richard L. Raymond
*Assistant Examiner*—Scott C. Rand
*Attorney, Agent, or Firm*—Edwin M. Szala; Ellen T. Dec

[57] ABSTRACT

A class of fluorinated phenylethynylaniline compounds is disclosed, said compounds having a use as capping reagents in high temperature stable polyimides or other polymers having a functionality which can undergo reaction with the amine to form a stable adduct. The diamine compounds of the invention are useful as step-growth monomers in the preparation of polymers containing reactive acetylene groups in the polymer backbone.

12 Claims, No Drawings

FLUORINATED ACETYLENE-CONTAINING AROMATIC AMINES AND DIAMINES

BACKGROUND AND PRIOR ART OF THE INVENTION

The present invention relates to fluorinated phenylethynylaniline (PEA) compounds. In a further aspect, this invention describes the preparation of fluorinated phenylethynylaniline compounds. Although these compounds are directed toward use as capping reagents in high temperature stable polyimides, they can be used for any polymer having suitable reactive functionality. Tis invention also relates to the preparation of fluorinated acetylene containing aromatic-diamines useful as monomers in step-growth polymerizations.

U.S. Pat. No. 4,594,352, issued June 10, 1986, discloses benzoyl-urea derivatives (derivatives of 1-benzoyl-3-aryl-urea) having high insecticidal activity. Two of the monoamine compounds of the cited patent are structural isomers of the compounds disclosed and claimed in the present invention. The key difference is that the compounds described in the present invention which are isomeric with those disclosed in U.S. Pat. No. 4,594,352 contain the amine nitrogen atom in a position which is meta to the acetylenic carbon, whereas the related prior art compounds contain the amine nitrogen in the para position. It is generally recognized by organic chemists that aryl acetylene compounds containing an electron donating group in the para position increases the rate of hydration of the acetylene to the corresponding ketone. Although hydration is normally carried out under acidic conditions in the presence of a mercuric salt, it has been shown to occur with p-aminophenylacetylenes (p-ethynylanilines) under the conditions of thermal imidization used to prepare certain polyimides. See Polymer Preprints, 21 (1), 81 (1980). Consistent with the intended use of these compounds (see formula I) as reactive capping reagents in which crosslinking occurs through the acetylene group, it is imperative that the acetylene moiety be resistant to hydration. Thus, it is a feature of the present invention that the m-substituted phenyl acetylene compounds herein are less subject to undesired hydration.

As stated above, the fluorinated acetylene containing amines of the invention are useful as capping reagents in any oligomer or polymer having functionality which can undergo reaction with the amine to form a stable adduct. The resulting aryl acetylene capped oligomer can be utilized, for example, as matrices in fiber reinforced composites or as the neat resin itself in the preparation of molded parts. Other uses include application in the microelectronics industry as an adhesive or coating. On further heating, the aryl acetylene undergoes a crosslinking reaction to give the final thermoset resin. The high temperature at which this reaction occurs provides a large window during which the oligomer or polymer can be processed in bulk. A detailed description of the use of these compounds as capping reagents is given in co-pending patent application (Ser. No. 07/482,362 filed Feb. 20, 1990) to C. Paul, et al.

The diamine compounds of the invention are useful as step-growth monomers in the preparation of polymers containing reactive acetylene groups in the polymer backbone which are capable of undergoing a further crosslinking reaction to give thermoset resins of high mechanical integrity. These monomers are particularly suitable in the preparation of thermally stable polyimides.

SUMMARY OF THE INVENTION

The present invention provides a new class of fluorinated phenylethynylaniline compounds having the general formula:

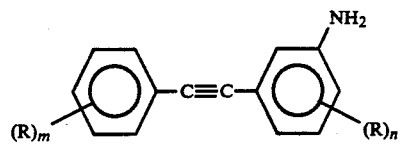

or

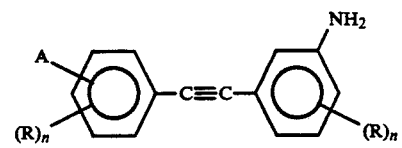

wherein R is H, F, $CF_3$, $CF_2CF_3$, $OCF_3$ or $SCF_3$; m is 1 to 5 and n is 1 to 4 and A is $NO_2$ or $NH_2$, provided that at least one R is fluorine or a fluorine-containing radical.

The compounds of the invention are crystalline solids, although some may be liquid at room temperature.

DESCRIPTION OF THE PREFERRED EMBODIMENTS

The subject capping reagents of this invention are prepared by a one step palladium catalyzed acetylene arylation reaction between aminophenylacetylene and a fluorinated aryl bromide. Alternatively, the arylation can be carried out on phenylacetylene utilizing an aryl bromide containing both fluoro and amino substituents on the same aromatic nucleus such as 2-amino-5-bromobenzotrifluoride. Appropriately substituted aryl iodides can also be employed in the same manner.

The subject diamine monomers of the invention can be prepared by several routes (methods). One such method involves the arylation of an amino phenylacetylene with a fluoro or fluoroalkyl substituted arylbromide, which is also nitro substituted on the same ring. Subsequent reduction of the nitro intermediate gives the target diamine. A one-step route which utilizes an arylation reaction between aminophenylacetylene and an amine substituted aryl bromide such as 2-amino-5-bromobenzotrifluoride can also be employed. As a third method, phenylacetylene can be employed instead of aminophenylacetylene when the fluorinated aryl bromide contains two amine functional groups such as 1,2-diamino-3-bromo-5-trifluoromethyl) benzene. In an extension of this route, the reaction may be carried out using the dinitro precursor to the diamine followed by selective reduction to yield the target diamine.

The acetylene arylation reaction is run in an inert atmosphere at atmospheric pressure at a temperature of 65°–85° C. for varying lengths of time, ranging from 6–48 hours, depending on the particular aryl bromide used in the reaction. The time and temperature required is dependent on the nature and position of other substituents on the aromatic nucleus of the aryl bromide. Reactants containing nuclear fluorine and/or amino substitution tend to require longer reaction times and higher catalyst to substrate ratios. This is partially offset by strongly electron withdrawing substituents such as nitro or trifluoromethyl. Triethylamine serves as both a solvent and scavenger for the hydrogen bromide generated during the reaction. Other useful amines which can be used in place of triethylamine are, for example, diethyl amine, butylamines, pyridine, and the like. A cosolvent such as toluene, xylene, dimethylformamide, or dimethylacetamide can also be used to improve the solubility of the reactants and/or product. The reaction requires the presence of a homogenous palladium catalyst which, for example, can be bis(triphenylphosphine)palladium (II) chloride or tetrakis(triphenylphosphine) palladium (O). To improve the utility of the palladium catalyst, an excess of the phosphine ligand is used. Examples of such phosphine ligands include triorthotoluylphosphine and triphenylphosphine which is preferred because of tis availability and cost. The use of palladium complexes to catalyze reactions of this type is described in the literature, for example, F. R. Heck and H. A. Dieck, J. Organometallic Chem., 93, p. 259-263 (1975). To further facilitate the reaction of co-catalyst may also be used. Suitable co-catalysts include cuprous salts, for example, cuprous chloride, cuprous bromide, and cuprous iodide which is preferred. The reaction is monitored by gas or thin layer chromatography, monitoring the disappearance of reactants and/or appearance of product.

The following examples which include the best mode of preparing the compounds will more fully illustrate the embodiments of this invention.

ANALYTICAL METHODS

Infrared (IR) spectra were recorded with a Digilab model FT8-80 FTIR using a TGS detector and 4 cm$^{-1}$ resolution. Differential Scanning Calorimetry (DSC) was obtained using a DuPont 912 dual cell module controlled by a DuPont 2100 programmer. A scanning rate of 10° C./min was utilized. The endothermic onset is the melting point of the compound and the corresponding heat of fusion is indicated after the endothermic onset in joules/grams. Mass spectrums were recorded with a HP-5993 GC/MS using a direction insertion probe when required. Carbon-13 nuclear magnetic resonance ($^{13}$C-NMR) were recorded on Either AM-300 or AC-250 Bruker spectrometers in deuterated chloroform using broad band proton decoupling. All chemical shifts (67) are reported in parts per million (ppm) relative to internal tetramethylsilane.

All compounds presented as examples have the diphenylacetylene moiety in the molecule. As substitution in a given compound may be present on one or both aromatic rings, the $^{13}$C-NMR data presented utilizes the numbering system shown below on the parent diphenylacetylene in making assignments.

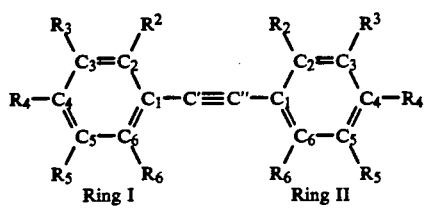

EXAMPLE 1

Preparation of 3-[[3-(Trifluoromethyl)phenyl]ethynyl]aniline

A multinecked round bottom flask fitted with a mechanical stirrer, reflux condenser, and thermometer was flushed and maintained under positive pressure of nitrogen. The flask was charged with 100.0 g (0.44 mol) of 3-bromobenzotrifluoride, 300 ml of dried, degassed triethylamine, 51.5 g (0.44 mol) of 3-aminophenylacetylene, 0.35 g (0.499 mmol) of bis(triphenylphosphine) palladium II chloride, 1.6 g (6.09 mmol) of (triphenylphosphine), and 0.1 g (0.52 mmol) of cuprous iodide. The reaction mixture was heated at 65° C. for 20 hours at which point gas chromatography showed the reaction to be complete. The product mixture was cooled to room temperature followed by the addition of 200 ml of ether. Removal of the triethylamine hydrobromide salt by-product by suction filtration followed by concentration of the filtrate under reduced pressure gave the crude product as a light off-white solid. Short path distillation of the crude product under reduced pressure gave 81.0 g (0.31 mol, 71% yield) of the product as a colorless liquid which crystallized on standing.

Analytical

C-NMR: δ87.0 (s, C''), 91.0 (s, C'), 123.6 (q, $J_{CF}$=273.0 Hz, ring I—$R_3$=$CF_3$), 130.7 (q, $J_{CCF}$=32.5 Hz, Ring I—$C_3$), 1146.1 (s, ring II—$C_3$) ppm.

Mass Spectrum: (70 eV), m/e 261 (M$^+$)

DSC: endothermic onset=57.2° C. (79 J/g), exothermic onset=340° C.

EXAMPLE 2

Preparation of 3-[(4-Fluorophenyl)ethynyl]aniline

A multinecked flask as described in Example 1 was charged with 50.0 g (0.28 mol) of p-bromofluorobenzene, 200 ml of dried, degassed triethylamine, 35.0 g (0.30 mol) of 3-aminophenylacetylene, 0.23 g (0.29 mmol) of bis(triphenyl phosphine) palladium II chloride, 1.03 g (3.92 mmol) of triphenylphosphine, and 0.1 g (0.52 mmol) of cuprous iodide. The reaction mixture was heated at 65° C. for 48 hours at which point gas chromatography showed the reaction to be complete. The mixture was cooled to room temperature and diluted with 200 ml of toluene. The toluene/triethylamine solution was decanted and concentrated on the rotary evaporator to give 75 g (0.27 mol, 96% yield) of the product as a bright yellow solid.

Analytical

C-NMR: δ87.0 s,C''), 89.3 (s,C'), 115.3 (s, ring I-$C_2$), 133.4 (s, ring I-$C_3$), 146.3 (s, ring II-$C_3$), 162.3 (d, $J_{CF}$=249.4 Hz, ring I-$C_4$) ppm.

Mass Spectrum: (70 eV), m/e 211 (M$^+$)

DSC: endothermic onset=80.3° C. (106 J/g), exothermic onset=375.8° C.

EXAMPLE 3

Preparation of 3-[[3-(Trifluoromethoxy)phenyl]ethynyl]aniline

A multinecked flask as described in Example 1 was charged with 5.0 g (0.021 mol) of m-bromophenyl trifluoromethyl ether, 50 ml of dried, degassed triethylamine, 2.43 g (0.212 mol) of 3-aminophenylacetylene, 0.048 g (0.68 mmol) of bis(triphenylphosphine) palladium II chloride, 0.148 g (0.564 mmol) of triphenylphosphine, and 0.03 g (0.157 mmol) of cuprous iodide. The reaction mixture was heated at 65° C. for 20 hours at which point gas chromotography showed the reaction to be complete. The product mixture was cooled to room temperature and diluted with 75 ml of ether. Filtration of the insoluble triethylamine hydrobromide salt by-product followed by concentration of the filtrate gave the crude product as a viscous orange-colored liquid. Short path distillation of the crude product under reduced pressure gave 5.1 g (0.018 mol, 86% yield) of the purified product as a colorless liquid.

Analytical

C-NMR: $\delta 87.1$ (s, C″), 91.1 (s, C′), 120.3 (q, $J_{CF}=257.5$ Hz, ring I-$R_3$=OCF$_3$), 146.5 (s, ring II-C$_3$), 148.8 s, ring I-C$_3$) ppm.

Mass Spectrum: 70 eV), m/e 277 (M+)

EXAMPLE 4

Preparation of 3-[(3,4-Difluorophenyl)ethynyl]aniline

A multinecked flask as described in Example 1 was charged with 5.0 g (0.026 mol) of 3,4-difluorobromobenzene, 50 ml of dried, degassed triethylamine, 3.0 g (0.026 mol) of 3-aminophenylacetylene, 0.07 g (0.1 mmol) of bis(triphenylphosphine) palladium II chloride, 0.1 g (0.38 mmol) of triphenylphosphine, and 0.02 g (0.1 mmol) of cuprous iodide. The reaction mixture was heated at 65° C. for 36 hours at which point gas chromatography showed the reaction to be complete. The product mixture was cooled to room temperature and diluted with 50 ml of ether. Filtration of the insoluble triethylamine hydrobromide salt by-product followed by concentration of the filtrate gave the crude product (4.2 g, 78% yield) as a off-white solid. Short path distillation of the crude product under reduced pressure gave 2.38 g (0.01 mol, 38% yield) of the purified product as a colorless liquid which crystallized on standing.

Analytical

C-NMR: $\delta 86.5$ (s, C″), 90.2 S, C′), 146.4 (s, ring II-C$_3$), 149.9 (dd, $J_{CF}=249.0$ Hz, ring I-C$_5$), 150.4 (dd, $J_{CF}=251.0$ Hz, ring I-C$_4$) ppm.

Mass Spectrum: (70 eV), m/e 229 (M+)

DSC: endothermic onset=89.9° C. (126 J/g), exothermic onset=365.4° C.

EXAMPLE 5

Preparation of 3-[(2,3,4,5,6-Pentafluorophenyl)ethynyl]aniline

A multinecked flask as described in Example 1 was charged with 5.0 g (0.020 mol) of bromopentafluorobenzene, 2.37 g (0.020 mol) of 3-aminophenylacetylene, 0.096 g (0.137 mmol) of bis(triphenylphosphine) palladium II chloride, 0.148 g (0.564 mmol) of triphenylphosphine, and 0.06 g (0.315 mmol) of cuprous iodide. The reaction mixture was heated at 70° C. for 40 hours after which gas chromatography showed the reaction to be complete. The product mixture was cooled to room temperature and diluted with 75 ml of ether. Filtration of the insoluble triethylamine hydrobromide salt by-product followed by concentration of the filtrate gave 5.7 g, (0.02 mol) of crude product as a yellow solid. Short path distillation of the crude under reduced pressure gave 2.84 g (0.010 mol, 50% yield) of the product as a colorless liquid that crystallized on standing.

Analytical

C-NMR: $\delta 72.3$ (s, C″), 100.1 (td, ring I-C$_1$), 102.1 (t, C′), 141.4 (d, ring I-C$_4$), 146.5 (s, ring II-C$_3$) ppm.

Mass Spectrum: (70 eV), m/e 283 M+)

DSC: endothermic onset=112.7° C. (89 J/g), exothermic onset=363.0° C.

EXAMPLE 6

Preparation of 4-[(3-Aminophenyl)ethynyl]-phenyl Trifluoromethyl Sulfide

A multinecked flask as described in Example 1 was charged with 5.4 g (0.021 mol) of p-bromophenyl trifluoromethyl sulfide, 75 ml of dried, degassed triethylamine, 2.46 g (0.021 mol) of 3-aminophenylacetylene, 0.048 g (0.068 mmol) of bis(triphenylphosphine) palladium II chloride, 0.0148 g (0.564 mmol) of triphenylphosphine, and 0.03 g (0.157 mmol) of cuprous iodide. The reaction mixture was heated at 75° C. for 20 hours after which gas chromatography showed the reaction to be complete. The mixture was cooled to room temperature and diluted with 75 ml of ether. Filtration of the insoluble triethylamine hydrobromide salt by-product followed by concentration of the filtrate gave the crude product in near quantitative yield as an off-white solid. Short path distillation of the crude product under reduced pressure gave 3.9 g (0.013 mol, 62% yield) of the purified product as a white solid.

Analytical

C-NMR: $\delta 87.4$ (s, C″), 92.4 (s,C′), 129.4 (q, $J_{CF}=308.4$ Hz, ring I-$R_4$=SCF$_3$), 146.1 (s, ring II-C$_3$) ppm.

Mass Spectrum: (70 eV), m/e 293 (M+)

DSC: endothermic onset=93.9° C. (98 J/g), exothermic onset=343.6° C.

EXAMPLE 7

Preparation of 3-[(2-Fluoro-5-(trifluoromethyl)phenyl]ethynyl]aniline

A multinecked flash as described in Example 1 was charged with 4.93 g (0.020 mol) of 3-bromo-4-fluorobenzotrifluoride, 75 ml of dried, degassed triethylamine, 2.34 g (0.020 mol) of 3-aminophenylacetylene, 0.06 g (0.08 mmol) of bis(triphenylphosphine) palladium II chloride, 0.118 g (0.45 mmol) of triphenylphosphine, and 0.06 g (0.31 mmol) of cuprous iodide. The reaction mixture was heated at 70° C. for 40 hours at which point gas chromatography showed the reaction to be complete. The product mixture was cooled to room temperature and diluted with 75 ml of ether. Filtration of the insoluble hydrobromide salt followed by concentration of the filtrate gave the crude product (5.5 g, 89%) as an orange liquid. Short path distillation of the crude product under reduced pressure gave 4.05 g (0.014 mol, 70% yield) of the product as a yellow solid.

Analytical

C-NMR: $\delta 80.5$ (s, C″), 93.4 (d, $J_{CCCF}=3.3$ Hz, C′), 113.2 (d, $J_{CCF}=17.0$ Hz, ring I-C$_1$), 123.9 (q, $J_{CF}=272.0$ Hz, ring I-$R_3$=CF$_3$), 164.2 (d, $J_{CF}=257.3$ Hz, ring I-C$_6$), ppm.

Mass Spectrum: (70 eV), m/e 279 (M+)

DSC: endothermic onset=54.2° C. (81 J/g), exothermic onset=341.1° C.

EXAMPLE 8

Preparation of 4-(Phenylethynyl)-2-(trifluoromethyl)aniline

A multinecked flask as described in Example 1 was charged with 10.0 g (0.042 mol) of 2-amino-5-bromobenzotrifluoride, 100 ml of dried, degassed triethylamine, 5.32 g (0.052 mol) of phenylacetylene, 0.48 g (0.41 mmol) of tetrakis(triphenylphosphine)palladium(O), 0.1 g (0.38 mmol) of triphenylphosphine, and 0.05 g (0.26 mmol) of cuprous iodide. The reaction mixture was heated at 70° C. for 48 hours at which point thin layer chromatography showed the reaction to be complete. The product mixture was cooled to room temperature and diluted with 50 ml of toluene. Filtration of the triethylamine hydrobromide salt by-product followed by concentration of the filtrate under reduced pressure gave the crude product as a yellow oil. Fractionation under reduced pressure (bp 146°–150° C./1.2 mm Hg) gave 7.22 g (0.028 mol, 66% yield) of the product as a viscous yellow oil.

Analytical

C-NMR: δ88.1 (s, C'), 88.6 (s, C''), 144.3 (broad single, ring II-$C_4$), 113.6 (q, $J_{CCF}$=30.4 Hz, ring II-$C_5$), 124.4 (q, $J_{CF}$=274.4 Hz, ring II-$R_5$=$CF_3$) ppm.

Mass Spectrum: (70 eV), m/e 261 (M+)

EXAMPLE 9

Preparation of 3-Amino-4'-fluoro-3'-nitrodiphenylacetylene

A multinecked flask as described in Example 1 was charged with 33.7 g (0.153 mol) of 3-bromo-6-fluoronitrobenzene, 300 ml of 10% (v/V) pyridine in triethylamine, 18.9 g (0.161 mol) of 3-aminophenylacetylene, 0.72 g (1.02 mmol) of bis(triphenylphosphine)palladium(II) chloride, 0.45 g (1.17 mmol) of triphenylphosphine, and 0.15 g (0.78 mmol) of cuprous iodide. The reaction mixture was heated at 50° C. for 18 hours at which point gas chromatography showed the reaction to be complete. After cooling to room temperature, the product mixture is diluted with 300 ml of ether and then filtered to remove the triethylamine hydrobomide (27.2 g, 89% of theory). The filtrate is concentrated under reduced pressure to give the product as an orange solid which can be further purified by recrystallization from heptane/toluene.

Analytical

C-NMR: δ85.1 (s, C''), 92.1 (s, C''), 92.1 (s, C'), 118.4 (d, $J_{CCF}$=21.5 Hz, ring I-$C_5$), 146.6 (s, ring II-$C_3$), 154.7 (d, $J_{CF}$=267.2 Hz, ring I-$C_4$) ppm.

IR; 2214 cm$^{-1}$ C≡C)

Mass Spectrum: (70 eV), m/e 256 M+)

DSC: endothermic onset=112.7° C. (87 J/g), exothermic onsets at both 174.4 and 294.4° C.

EXAMPLE 10

Preparation of 3,3'-Diamino-4-fluorodiphenylacetylene

A multinecked flask as described in Example 1 was charged with 5.0 g (0.02 mol) of 3-amino-4'-fluoro-3'-nitrodiphenylacetylene; 25 ml of ethyl alcohol, and 30 g (0.13 mol) of tin (II) chloride dihydrate. The resulting orange slurry was cooled to 0° C. followed by portionwise addition of 55 g (0.54 mol) of concentrated hydrochloric acid. The reaction mixture was then heated at mild reflux for 16 hours followed by dilution with 100 ml of distilled water. After neutralization with 25% aqueous sodium hydroxide, the crude product was extracted with three 50 ml portion of toluene. The toluene extracts were dried over anhydrous sodium sulfate and concentrated to give 3.61 g (0.016 mol, 84% yield) of the product as a yellow solid.

Analytical

C-NMR: δ88.3 (s, C''), 88.6 (s, C'), 134.6 (d, $J_{CCF}$=13.5 Hz, ring I-$C_3$), 146.4 (s, ring II-$C_3$), 151.6 (d, $J_{CF}$=242 Hz, ring I-$C_4$) ppm.

Mass Spectrum: (70 eV), m/e 226 (M+)

DSC: endothermic onset=104.7° C. (86 J/g), exothermic onset=277.4° C.

EXAMPLE 11

Preparation of 3-Amino-4'-nitro-2'-(trifluoromethyl)diphenylacetylene

A multinecked flask as described in Example 1 was charged with 10.0 g (0.037 mol) of 2-bromo-5-nitrobenzotrifluoride, 100 ml of dry triethylamine, 4.56 g (0.030 mol) of 3-aminophenyl-acetylene, 0.030 g (0.04 mmol) of bis(triphenylphosphone)palladium(11)chloride, 0.133 g (0.51 mmol) of triphenylphosphine, and 0.027 g (0.14 mmol) of cuprous iodide. The reaction mixture was heated at 60°–65° C. for 18 hours at which point thin layer chromatography showed the reaction to be complete. After cooling to room temperature, the product mixture is diluted with 100 ml of 25% (v/v) toluene in ether and then filtered to remove the triethylamine hydrobromide by-product. The filtrate is concentrated on the rotary evaporator to give the product in quantitative yield as a bright yellow solid. The product can be further purified by recrystallization from aqueous ethanol.

Analytical

C-NMR: δ83.4 (s, C''), 101.4 (s, C'), 122.3 (q, $J_{CF}$=274.1 Hz, ring I-$R_2$=$CF_3$), 132.6 (q, $J_{CCF}$=32.1 Hz, ring I-$C_2$) ppm.

IR: 2213 cm$^{-1}$ (C≡C, strong)

Mass Spectrum: (70 eV) m/e 306 (M+)

DSC: endothermic onset=164.5° C. (97.3 J/g), exothermic onset=322° C.

EXAMPLE 12

Preparation of 3,4'-Diamino-2'-(trifluoromethyl)diphenylacetylene

A 2-liter titanium pressure reactor equipped with inlet/outlet ports regulated with stainless steel needle valves, rupture disc, thermocouple well, pressure gauge, and a sealed magnetic drive stirrer was charged with 5.0 g (0.016 mol) of 3-amino-4'-nitro-2'0(trifluoromethyl)-diphenylacetylene, 260 ml of 3.8% (V/V) aqueous methanol, 0.34 g of triphenylphosphine, and 1.25 g of 5% ruthenium on alumina. The reactor is pressurized with hydrogen to a concentration of 50 psi and maintained at that pressure until reduction is complete as judged by thin layer chromatography. The ruthenium catalyst is removed by filtration and the filtrate concentrated on the rotary evaporator. The concentrate is dissolved in benzene and dried over anhydrous sodium sulfate. The sodium sulfate is removed by filtration and the filtrate concentrated to give 4.3 g (0.015 mol, 96% yield) of the product as viscous orange oil. Crystallization from benzene/cyclohexane affords the product (3.3 g, 73%) as yellow needles.

Analytical

C-NMR: δ88.5 (s, C″), 92.5 (s, C′), 123.6 (q, $J_{CF}$=273.8 Hz, ring I−R$_2$=CF$_3$), 132.8 q, $J_{CCF}$=30.1 Hz, ring I−C$_2$), 146.3 (s, ring 11−C$_3$) ppm.

Mass Spectrum: m/e 276 (M+)

DSC: endothermic onset=89.4° C. (96.4 J/g), exothermic onset=277.4° C.

The practitioner will understand that an extension of the chemistry disclosed and described herein is to carry out the acetylene arylation on fluorinated aryl bromides containing further aromatic substitution such as, for example, 4-bromo-2-fluorobiphenyl.

Now that the preferred embodiments of the present invention have been described in detail, various modifications and improvements thereon will become readily apparent to those skilled in the art. Accordingly, the spirit and scope of the invention are to be limited only by the appended claims and not by the foregoing specifications.

what is claimed is:

1. A compound of the formula

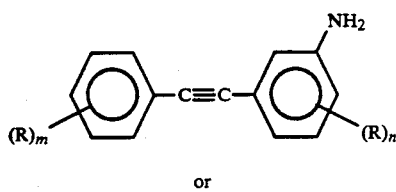

or

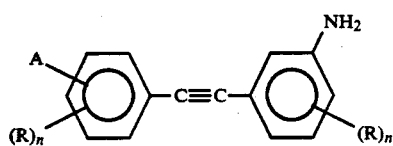

wherein R is H, F, CF$_3$, CF$_2$CF$_3$, OCF$_3$ or SCF$_3$, m is 1 to 5 and n is 1 to 4 and A is NO$_2$ or NH$_2$; provided that at least one R is fluorine or a fluorine-containing radical.

2. A compound of the formula

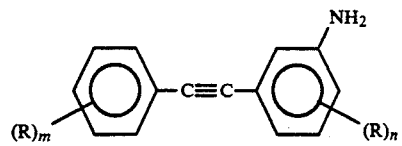

wherein R is H, F, CF$_3$, OCF$_3$ or SCF$_3$; m is 1 to 5 and n is 1 to 4 provided that at least one R is fluorine or a fluorine-containing radical.

3. A compound of claim 2 which is 3-[[3-(trifluoromethyl)phenyl]ethynyl]aniline.

4. A compound of claim 2 which is 3-[4-fluorophenyl)ethynyl]aniline.

5. A compound of claim 2 which is 3-[[3-(trifluoromethoxy)phenyl]ethynyl]-aniline.

6. A compound of claim 2 which is 3-[(3,4-difluorophenyl)ethynyl]aniline.

7. A compound of claim 2 which is 3-[(2,3,4,5,6-pentafluorophenyl)ethynyl]-aniline.

8. A compound of claim 2 which is 4-[2,3-aminophenyl)ethynylphenyl trifluoromethyl sulfide.

9. A compound of the formula

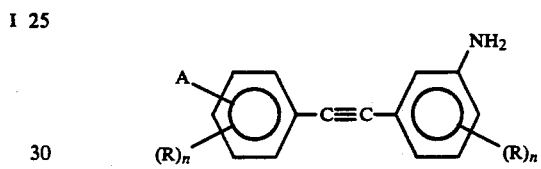

wherein R is H, F, CF$_3$, CF$_2$CF$_3$, OCF$_3$ or SCF$_3$, n is 1 to 4, and A is NO$_2$ or NH$_2$, provided that at least one R is fluorine or a fluorine-containing radical.

10. A compound of claim 9 which is 3-amino-4′-fluoro-3′-nitrodiphenylacetylene.

11. A compound of claim 9 which is 3,3′-diamino-4-fluorodiphenylacetylene.

12. A compound of claim 9 which is 3-amino-4′-nitro-2′-(trifluoromethyl)diphenylacetylene or 3,4′-diamino-2′-(trifluoromethyl)diphenylacetylene.

* * * * *